United States Patent [19]

Schroeppel

[11] Patent Number: 5,228,437
[45] Date of Patent: Jul. 20, 1993

[54] CARDIAC PACEMAKER AND METHOD FOR DETECTING CARDIAC SIGNALS

[75] Inventor: Edward A. Schroeppel, Lake Jackson, Tex.

[73] Assignee: Intermedics Orthopedics, Inc., Angleton, Tex.

[21] Appl. No.: 696,160

[22] Filed: May 6, 1991

[51] Int. Cl.⁵ .............................................. A61N 1/362
[52] U.S. Cl. .............................................. 128/419 PG
[58] Field of Search ................................. 128/419 PG

[56] References Cited

U.S. PATENT DOCUMENTS

| | | | |
|---|---|---|---|
| 4,114,627 | 9/1978 | Lewyn et al. | 128/419 PG |
| 4,343,312 | 8/1982 | Cals et al. | 128/419 PG |
| 4,399,818 | 8/1983 | Money | 128/419 PG |
| 4,498,478 | 2/1985 | Bourgeois | 128/419 PG |
| 4,759,366 | 7/1986 | Callaghan | 128/419 PG |
| 4,821,724 | 4/1989 | Whigham et al. | 128/419 PG |

FOREIGN PATENT DOCUMENTS

| | | |
|---|---|---|
| 0043690 | 1/1982 | European Pat. Off. . |
| 0057944 | 8/1982 | European Pat. Off. . |
| 0147292 | 7/1986 | European Pat. Off. . |
| 0246908 | 11/1987 | European Pat. Off. . |
| 0393404 | 10/1990 | European Pat. Off. . |
| 2193101 | 2/1988 | United Kingdom . |
| 8909514 | 10/1989 | World Int. Prop. O. . |

Primary Examiner—William E. Kamm
Attorney, Agent, or Firm—John R. Merkling

[57] ABSTRACT

An apparatus for detecting an electrical potential in a human body to control the delivery of a therapy. The electrical potential comprises a principal signal and a baseline signal. The apparatus samples the potential through an electrode during a selected interval and stores the value of that potential at the end of the interval. The stored value of the potential will be restored as an initial condition on the electrode at the end of a second interval after delivery of the therapy. In a heart pacemaker, the baseline signal is useful for controlling the output pulses of the pacemaker. The apparatus permits sensing of the baseline signal despite stimulating pulses and charge canceling.

12 Claims, 3 Drawing Sheets

CARDIAC PACEMAKER AND METHOD FOR DETECTING CARDIAC SIGNALS

FIELD OF MY INVENTION

My invention relates to implantable therapeutic devices having electrodes carried on leads, and in particular to implantable cardiac pacemakers. More specifically, my invention relates to a cardiac pacemaker having an electrode on an implanted lead adapted to perform multiple functions through the same electrode; for example, the function of pacing the heart and the function of measuring a parameter indicative of the physiologic condition of the patient or the patient's heart.

BACKGROUND OF MY INVENTION

Many therapeutic devices use electrodes to measure electrical potentials at selected locations in a human body. Electrodes have been used to measure electric signals relating to chemical concentrations, nerve activity, respiration rate, or cardiac rhythms, as examples. Cardiac pacemakers, for example, stimulate the heart with electrical impulses to induce a heartbeat. Pacemakers may also sense the condition of the heart so that stimuli may be applied in an appropriate manner. Electrodes on a lead of a cardiac pacemaker may be used to measure features of the intracardiac electrogram, lead or tissue impedance, pH of the blood and other parameters. In addition to the desired, information carrying signals, the electrode may detect unwanted signals such as remote or far field signals, noise, muscle activity potentials and so on. The sense electrode or another electrode may be used to stimulate a physiological mechanism by an appropriate signal; for example, stimulating the heart to induce a heartbeat. Such a stimulation can result in a residual polarization voltage which masks the desired signal.

Accurate signal detection through an implanted electrode continues to present difficulties for the designer of an implanted therapeutic device. In some applications, it may be desired to detect one or more input signals and to apply one or more stimulating or output signals. At the same time, it may be inadvisable to employ a dedicated electrode for each operation. The desired size of a lead may limit the number of conducting wires which can practically be connected to separate electrodes or the number of electrodes themselves may be limited. Moreover, interelectrode cross-talk between separate electrodes may limit the usefulness of separate electrodes.

To solve these problems, time multiplexing of an electrode has heretofore been employed. The same electrode used to output a stimulating pulse during a first interval may be employed to sense cardiac signals during another interval and noise or some other parameter during yet another interval. Bandpass filtering has been used to discriminate between desirable signals and noise. These methods, however, are not effective in all cases. Unwanted signals may mask desired signal in certain applications. In other applications, a signal of interest may mask another signal of interest, requiring the rejection of the first signal in order detect the second.

With the foregoing in mind, it is an object of my invention, therefore, to provide an apparatus and method for an implanted therapeutic device having an electrode which can be used for multiple functions.

It is also an object of my invention to provide an apparatus and electrode which can be used for both input and output functions.

Another object of my invention is to provide an implanted apparatus which can extract information from a background signal during a selected interval despite the presence of a primary signal which tends, during another time interval, to influence the electrode potential to destroy the electrode's ability to sense the background signal.

SUMMARY OF MY INVENTION

I have invented an apparatus which measures an electrical potential characteristic of a parameter during a selected interval and stores the value of that potential at the end of the interval. During a successive interval, an intervening event may occur to seriously disrupt the potential. This intervening event may be either an intrinsic potential caused by the human body or an external stimulation; for example, a stimulus from a pacemaker. If such an intervening event occurred during the second time interval, the stored value of the measured potential will be restored as an initial value at the end of the second interval.

Apparatus, according to my invention, includes a timing circuit to identify appropriate intervals. Control circuitry or software is provided to determine if conditions have occured which require potential restoration. Means are provided for sampling and storing the value of the electric potential at a given time and for restoring the measured potential to an electrode at a second selected time. The means may include electrical circuitry or software and may employ either analog circuitry or analog to digital conversion with digital registers or memory circuitry. Algorithms to establish appropriate responses to detected noise or other classes of signals may also be provided.

My invention may be employed with electrodes generally, including physiological, chemical, physical, or other electrodes. It may also be used to set the initial potential conditions of one electrode with reference to a detected condition at another electrode.

These and other objects and features of my invention will be apparent to those skilled in the art from the following detailed description of my preferred embodiment, made with reference to the accompanying drawings.

DETAILED DESCRIPTION OF MY PREFERRED EMBODIMENT

I will now describe my preferred embodiment of my invention. In referring to the accompanying figures, like numerals will be used to refer to like parts throughout this description. Although I have chosen to describe my invention in terms of a implanted cardiac pacemaker, those skilled in the art will recognize that my invention can be applied to measure electric potentials in many applications.

Figure 1:
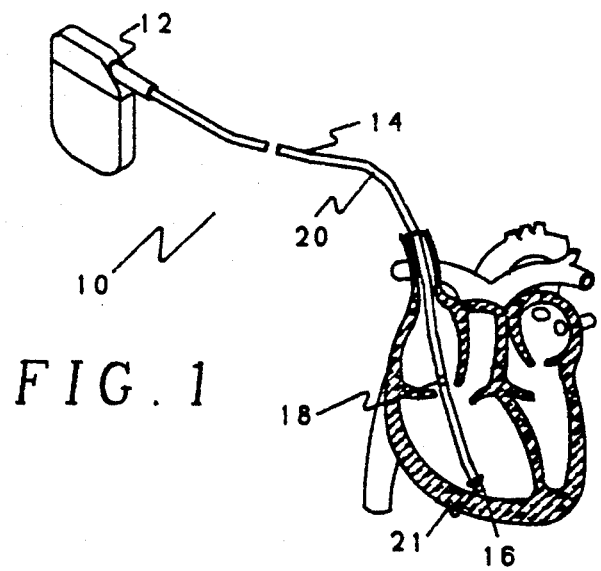
FIG. 1 is perspective view of a cardiac pacemaker system according to my present invention with a cardiac pacemaker and a lead, showing placement of the lead in a cutaway section of a human heart.

In FIG. 1, a perspective view of a cardiac pacemaker system, generally designated 10, is shown in perspective view. A cardiac pacemaker 12 is provided having the capacity to sense electrical artifacts at sense electrodes within a heart. A lead 14 is shown connected to the pacemaker 12. In the illustrated embodiment, the lead is illustrated as having a distal electrode 16 at a distal end of the lead. As is known in the art, fixation means should generally be provided. I have illustrated tines 21. The distal electrode 16 may be used for both sensing and stimulating the heart in accordance with my present invention. An additional ring electrode 18 is shown within the atrium of the heart. The ring electrode 18 may also be used for multiple purposes and employed with the apparatus of my present invention. It will be apparent that the number of electrodes employed in the invention is not limited.

Figure 2:
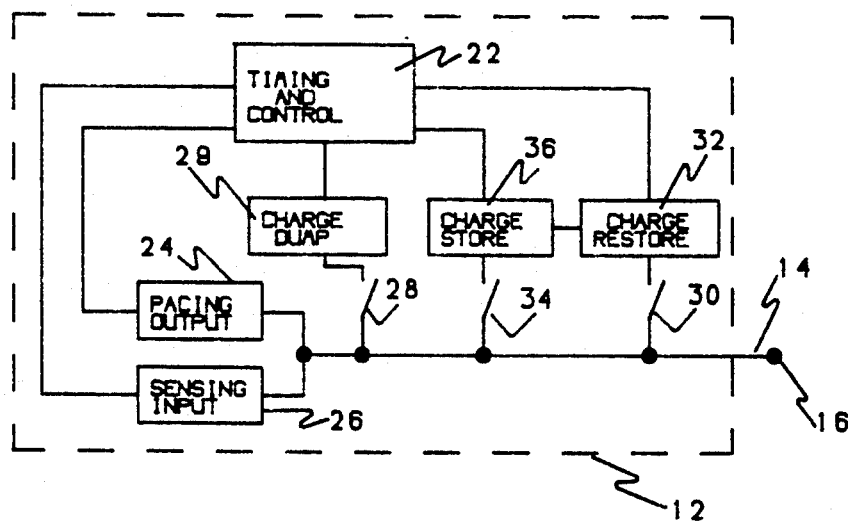
FIG. 2 is a block diagram of a heart pacemaker employing apparatus according to my invention.

FIG. 2 illustrates a block diagram of the cardiac pacemaker 12 showing the apparatus of my present invention. The lead 14 and the distal tip 16 are illustrated. Additional connections may be provided for additional electrodes, such as electrode 18. Timing and control circuitry 22 controls control pacing output circuitry 24 to provide stimulating pulses to the heart and, at appropriate times, receive signals from sensing input circuitry 26 from the heart. Multiplexing between pacing and sensing are known in the pacemaker art and need not be described in greater detail herein. Sensed signals may comprise the heart's QRS complexes, polarization potentials on the electrode 16, noise from electromagnetic sources or from muscles of the body, or various physiological parameters such as respiration, pH and so on. Timing and control circuitry 22 may be implemented by those skilled in the art in either electrical hardware or a combination of hardware and software.

Under the control of the timing and control circuitry 22, a first switch 28 closes briefly after an output pulse is delivered from the pacing output circuitry 24. Closing of the first switch 28 connects the electrode 16 to ground or charge dump 29. The timing and control circuitry 22 may then begin to time out a physiological parameter sampling interval for a predetermined length of time. At the beginning of the sampling interval, the timing and controlling circuitry closes a restore switch 30 which connects a charge restore circuit 32 to the electrode 16. The charge restore circuit 32 is effective to restore the electrical condition of the electrode to the condition of that electrode at the end of the last preceding sampling interval. The charge control circuit 32 may be implemented by a storage capacitor and analog circuitry or by digital circuitry with a digital to analog converter.

The timing and control circuitry 32 then activates the sensing input 26 to measure the desired electrical potential at the electrode 16 during the sampling interval. At the end of the sampling interval, the timing and control circuitry 22 briefly closes a charge store switch 34 and stores the value of the potential of the electrode 16 in charge store circuit 36. As with the charge restore circuit 32, the charge store circuit may comprise analog or digital circuitry. Any anticipated losses to the electrode potential occurring in either potential measurement, charge storage or restoration are compensated in transferring the charge store circuit 36 to the charge restore circuit 32.

Figure 3:
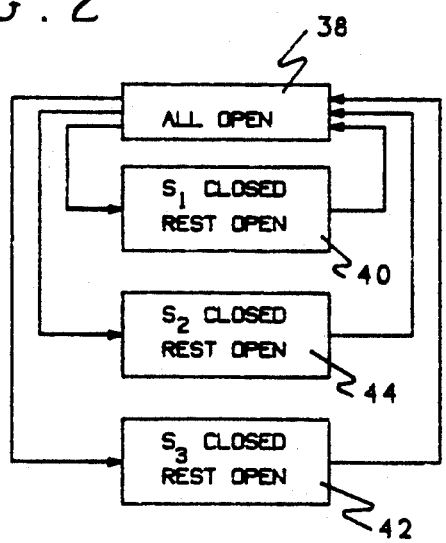
FIG. 3 is a logic diagram for describing timing of switches according to my present invention.

Control of the switches 28, 30 and 34 can also be understood with reference to the logic diagram of FIG. 3. Under the control of the timing and control circuit 22, all switches are normally open 38. Before attempting to restore the electrical condition of the electrode 16, as, for example, after a stimulating pulse from the pacing output circuitry 24, first switch 28 closes 40, connecting the electrode to ground and then quickly reopens. Just before the sampling interval and after switch 28 has been closed, the charge restore switch 30 closes 42, allowing charge restore circuitry 32 to charge the electrode 16 to the predetermined electrical condition. The electrical condition of the electrode is relatively quickly restored and then switch 30 again reopens. Just before the end of the sampling interval, the charge store switch 34 is closed 44 connecting the charge store circuit 36 to the electrode. The electrical condition of the electrode is rapidly sampled over a very short interval and the switch 34 is again opened.

Figure 4:
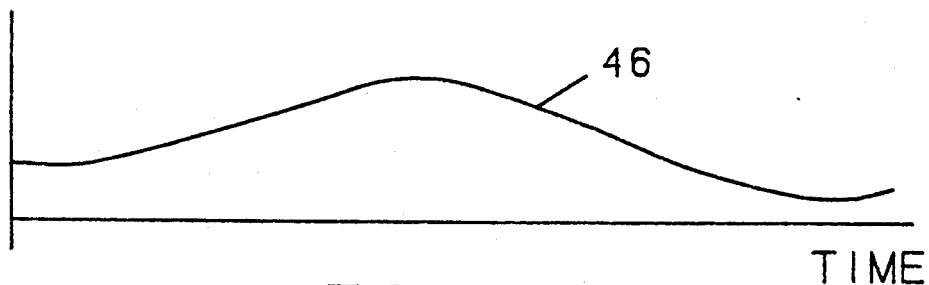
FIG. 4 is a graph of a potential varying over time.

I will now explain the operation of my invention with reference to the graphs of FIGS. 4 through 11. FIG. 4 illustrates an exemplary electrical potential 46 which varies in amplitude over time. The electrical potential is the signal which is to be measured or detected by an electrode. This does not imply, however, that the potential 46 is the only electrical signal present. There may be other signals, extraneous noise, or, in the case of a heart pacemaker, output signals or stimulating pulses which mask or make the measurement of the potential 46 more difficult.

Figure 5:
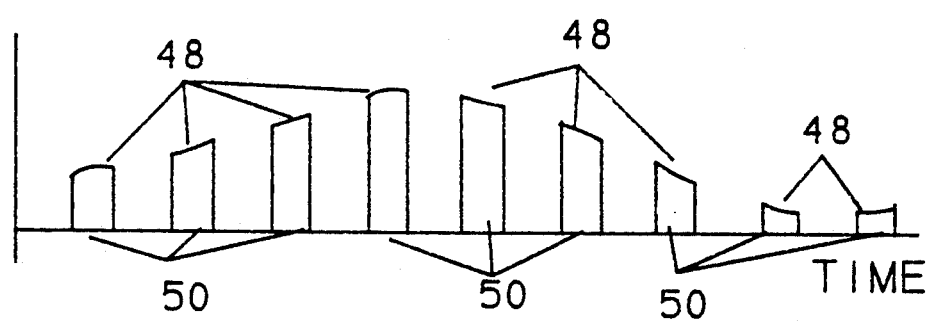
FIG. 5 is the potential of FIG. 4 sampled at selected intervals.
Figure 6:
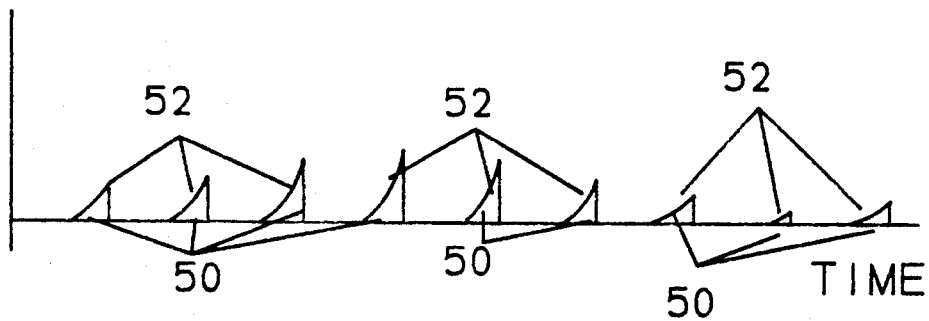
FIG. 6 is a graph of a sampling of the potential of FIG. 4 with the potential forced to zero at the beginning of each interval.

FIG. 5 shows an idealized measurement of the potential 46 by a multiplexed electrode. As the electrode 16 is multiplexed to its sensing function, potential segments 48 are sensed during selected intervals 50. In the desired situation, the potential segments 48 closely approximate the potential 46 and meaningful information about the potential 46 can be extracted from the potential segments 48. With uncompensated multiplexing alone, however, the wave form of FIG. 5 is seldom, if ever, retrieved. This is because the initial conditions of the segments 48 in reality do not correspond to the initial conditions of each segment as shown in FIG. 5. Rather, each segment begins at some other value and only approaches the true value for the segment. Such a condition is illustrated in FIG. 6. At the beginning of each time segment 50 the value of the measured potential is constrained to be zero. Such a condition might occur if the electrode were grounded immediately before the beginning of the time segment 50. Those skilled in the art will recognize, of course, that the zero initial condition is chosen only as an example because of its simplicity and clarity. Any other initial condition, constant or varying, which was not related to the desired signal 46, would have the same negative effect. Because of the inherent time constants of the system, during each measurement 50 a measured segment of potential 52 will only begin to approximate the true value of the potential 46. A great deal of information about the potential 46 could be lost, resulting in potentially erroneous responses by an implanted device such as a cardiac pacemaker.

Figure 7:
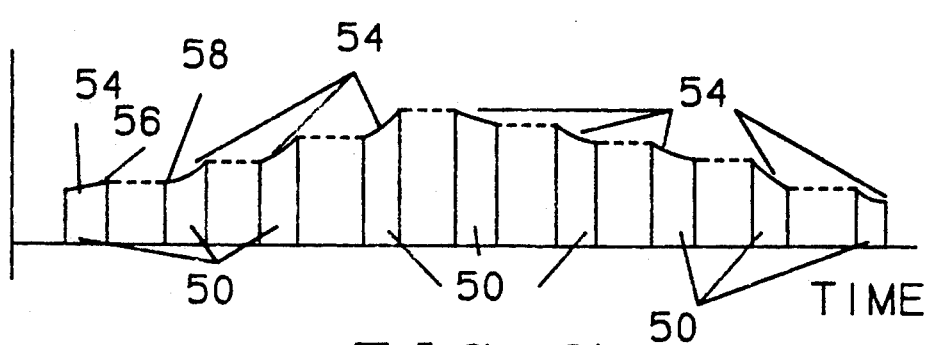
FIG. 7 is a sampling of the potential of FIG. 4 with the terminal conditions of each sampled interval imposed on the succeeding sample interval as initial conditions.

In a device with apparatus and methods according to my invention, the wave form of FIG. 7 would be recovered. During each time segment 50, the magnitude of the measured potential would more closely approximate the true potential 46. At the end 56 of a potential segment 54, the magnitude or other parameter of the potential would be stored. At a beginning 58 of the next succeeding segment 54, the ending value at 56 would be restored to the electrode. Measurement would then begin and the potential on the electrode would begin to approach the true value of the potential 46, constrained by the inherent time constants of the particular system. Since it is likely, however, that the value at the end of the last measuring period more closely approximates the true value at the beginning of the next succeeding period than would an arbitrary value such as zero, the measurement of potential, as shown in FIG. 7, would more closely approximate the idealized measurements of FIG. 5 and thus be a better representation of the true potential shown in FIG. 4.

Figure 8:
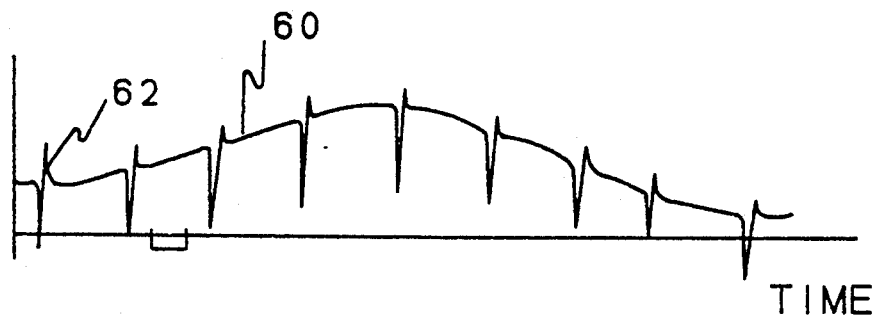
FIG. 8 is a graph of an electric potential comprising a potential similar to that shown in FIG. 4 combined with an intrinsic cardiac depolarization signal.

FIGS. 8 through 11 illustrate an application of my invention in the field of cardiac pacing. FIG. 8 shows a signal 60 similar to the potential 46 of FIG. 4 but with the addition of an intrinsic intracardiac QRS signal 62 at periodic intervals. Such a signal 62 would be detected on an electrode in the right ventricle of a typical healthy heart. The intrinsic QRS signals 62 are essentially added to the underlying baseline potential 46 shown in FIG. 4. To extract the baseline potential a low pass filter or sampling method analogous to that illustrated in FIG. 5 might be employed. Under such circumstances filtering and sampling would be adequate to extract the desired information.

Figure 9:
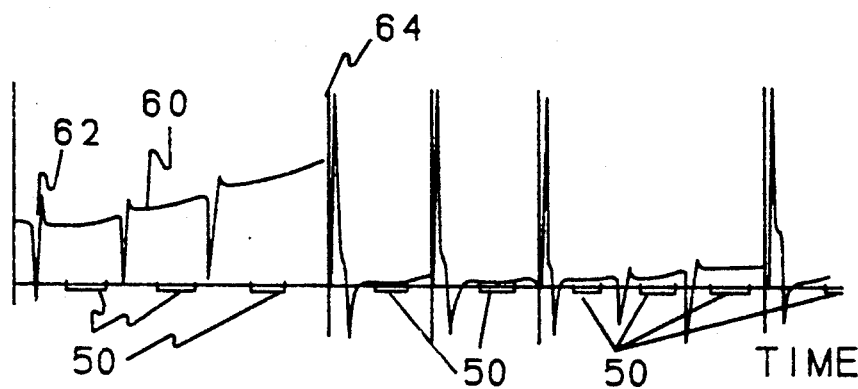
FIG. 9 is a graph of the potential of FIG. 8 combined with stimulating cardiac pacing pulses.

If a cardiac pacemaker is present, however, additional complications are introduced. FIG. 9 illustrates the result of cardiac pacing on a prior art bandpass and sampling electrode. A pacing pulse 64 and resulting depolarization disrupts the measurement of the signal 60. Charge dumping, a known technique used to reduce lead polarization potential, tends to force the voltage at the electrode to zero after each pulse. The sampling of the underlying baseline potential occurs during the intervals between pulses. Because of the pacing, the sampling intervals 50 may tend to occur irregularly over time, being associated with a delay after the pacing pulse. Moreover, charge dumping removes the baseline information and distorts the sample values. Over time, of course, the baseline will return to its natural value but during the time period surrounding a series of paper pulses, significant amounts of information will be lost.

Figure 10:
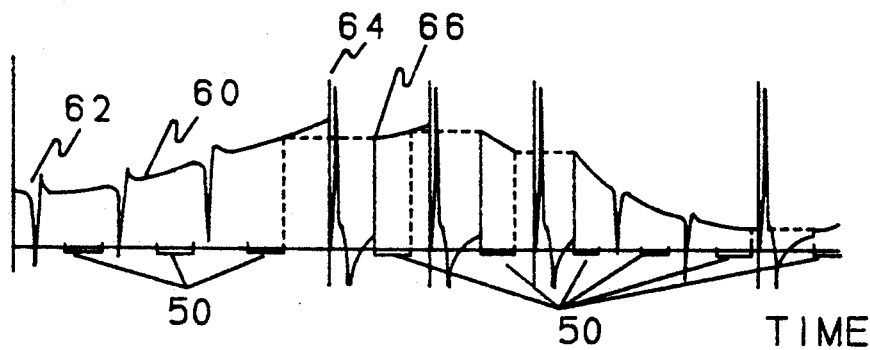
FIG. 10 is a potential including the potential of FIG. 9 combined with restoration of initial conditions according to my present invention.
Figure 11:
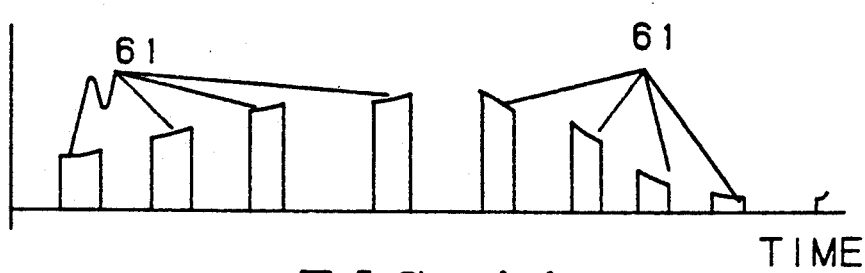
FIG. 11 is the potential of FIG. 10 with the cardiac pulses and stimulating pulses eliminated.

Employing my invention, however, tends to restore the information regarding the baseline 60. As seen in FIG. 10, the ending condition of one segment is restored at 66 to the next time segment. The baseline can be much more closely approximated. FIG. 11 extracts an approximation 61 of the baseline information from FIG. 10 and omits the pacer pulses and intrinsic QRS waves. A comparison between this waveform and the waveform of FIG. 8 or FIG. 4 illustrates that a closer approximation of the baseline potential can be expected.

It will be apparent to those skilled in the art that my invention can be embodied in other configurations without departing from the teachings or essential characteristics thereof. The foregoing description is, therefore, to be considered illustrative and not restrictive and the scope of my invention is to be defined by the following claims. All changes or variations that would come within the equivalency of the claims are intended to be incorporated therein.

I claim as my invention:

1. An apparatus for delivering a controlled therapy to a human body in response to a detected electrical potential comprising a principal signal and a baseline signal, said apparatus comprising
   an electrode adapted to be connected to said human body to detect said electrical potential;
   timing means for timing a series of first and second intervals;
   means for sensing said electrical potential during said first intervals;
   means for storing the magnitude of said baseline potential at the end of said first intervals;
   means responsive to said principal signal and said baseline signal for delivering said therapy to said human body during selected second intervals;
   means for canceling an electrical after-effect of said therapy during said selected second intervals; and
   means for recreating the stored magnitude of said baseline signal at said electrode at the end of said second intervals.

2. The apparatus according to claim 1 further comprising means for compensating for expected losses in recreating the stored value of said baseline signal.

3. The apparatus according to claim 1 further comprising a ground potential and wherein said canceling means comprise means for connecting the electrode to said ground potential prior to recreating the stored value of the electrical potential.

4. The apparatus according to claim 1 further comprising a plurality of switches, at least one switch selectively connecting and disconnecting each of the storing means, the recreating means, and the canceling means to said electrode and wherein said timing means further comprises means for controlling said switches to connect said storing means to said electrode at the end of said first intervals, said recreating means at the end of said second intervals, and said canceling means during said second intervals.

5. A heart pacemaker comprising
   means for generating stimulating pulses of electrical charge for application to the heart of a patient;
   a lead adapted to connect said pacemaker to the heart;
   at least one electrode on said lead;
   means for sensing an electrical potential in the heart, said electrical potential comprising a baseline potential and periodic QRS signals, said sensing means comprising
   means for canceling the charge of said stimulating pulses,
   means for sensing said QRS signals,
   timing means for timing a series of first and second intervals;
   means for sensing said baseline potential during said first intervals;

means remote from said electrode for storing the magnitude of said baseline potential at the end of said first intervals; and means for recreating at said electrode the stored magnitude of said baseline potential at the end of said second intervals; and means responsive to said electrical potential sensing means for pacing the heart as a function of said sensed QRS signals and said sensed baseline potential.

6. The heart pacemaker according to claim 5 further comprising means for compensating for expected losses in recreating the stored magnitude of said baseline potential.

7. The heart pacemaker according to claim 5 wherein said pacemaker further comprises a ground potential and wherein said means for canceling the charge of said stimulating pulses further comprise means for connecting the sensing means to said ground potential prior to recreating the stored magnitude of the baseline potential at said electrode.

8. The heart pacemaker according to claim 5 further comprising a plurality of switches, at least one switch selectively connecting and disconnecting each of the storing means, the recreating means, and the charge canceling means to said electrode and wherein said timing means further comprises means for controlling said switches to connect said storing means to said electrode at the end of said first intervals, said recreating means at the end of said second intervals, and said charge canceling means during said second intervals.

9. A method for pacing a human heart comprising the steps of
timing a series of first and second intervals;
detecting said electrical potential through an electrode during said first intervals said electrical potential comprising a series of QRS signals and a baseline potential;
storing the magnitude of said baseline potential at the end of said first intervals;
selectively pacing the heart during said second interval;
canceling a charge created at said electrode by said pacing;
recreating the stored value of said baseline potential at the end of said second intervals.

10. The method for pacing a human heart according to claim 9 further comprising compensating for expected losses in recreating the stored value of said baseline potential.

11. The method for pacing a human heart according to claim 10 wherein the charge canceling step comprises connecting said electrode to a ground potential prior to recreating the stored value of the electrical potential.

12. The method for pacing a human heart according to claim 11 further comprising selectively connecting and disconnecting storing means, recreating means, and ground connecting means to said electrode.

* * * * *

UNITED STATES PATENT AND TRADEMARK OFFICE
CERTIFICATE OF CORRECTION

PATENT NO. : 5,228,437

DATED : July 20, 1993

INVENTOR(S) : Edward A. Schroeppel

It is certified that error appears in the above-identified patent and that said Letters Patent is hereby corrected as shown below:

On the title page, the Assignee should read:
"Intermedics Orthopedics, Inc." should read -- Intermedics, Inc. --

Signed and Sealed this

Eleventh Day of April, 1995

Attest:

BRUCE LEHMAN

Attesting Officer

Commissioner of Patents and Trademarks